US005348556A

United States Patent [19]

Minns et al.

[11] Patent Number: 5,348,556

[45] Date of Patent: Sep. 20, 1994

[54] VOLATILE CARPET SANITIZING SHAMPOO CONTAINING HYDROGEN PEROXIDE

[75] Inventors: Charles R. Minns, Williamsburg; Timothy W. Blount, Poquoson; Thomas L. Varner, Jr., Williamsburg, all of Va.

[73] Assignee: BASF Corporation, Parsippany, N.J.

[21] Appl. No.: 145,053

[22] Filed: Oct. 27, 1993

Related U.S. Application Data

[63] Continuation of Ser. No. 887,446, May 21, 1992, abandoned, which is a continuation-in-part of Ser. No. 650,353, Feb. 4, 1991, abandoned, which is a continuation-in-part of Ser. No. 462,919, Jan. 8, 1990, Pat. No. 5,252,243, which is a continuation of Ser. No. 206,531, Jun. 14, 1988, abandoned.

[51] Int. Cl.[5] .......................... A61L 2/16; C11D 7/18; C11D 7/50; D06L 1/12

[52] U.S. Cl. .......................................... 8/137; 8/111; 252/102; 252/103; 252/104; 252/106; 422/28

[58] Field of Search .................... 8/111, 137; 252/102, 252/103, 104, 106; 422/28

[56] References Cited

U.S. PATENT DOCUMENTS

| | | | |
|---|---|---|---|
| 3,144,297 | 8/1964 | Kinder | 8/111 |
| 3,227,655 | 1/1966 | Prett | 252/102 |
| 3,607,760 | 9/1971 | McIntyre | 252/104 |
| 3,651,931 | 3/1972 | Hsiung | 8/111 |
| 3,686,126 | 8/1972 | Smeets | 252/99 |
| 3,811,833 | 5/1974 | Stalter | 8/111 |
| 3,904,361 | 9/1975 | Egger | 21/57 |
| 4,347,149 | 8/1982 | Smith et al. | 252/102 |
| 4,490,270 | 12/1984 | Hackett et al. | 252/106 |
| 4,497,725 | 2/1985 | Smith et al. | 252/102 |
| 4,512,951 | 4/1985 | Koubek | 422/33 |
| 4,557,898 | 12/1985 | Greene et al. | 422/28 |
| 4,783,194 | 11/1988 | Dugenet | 8/111 |
| 4,943,414 | 7/1990 | Jacobs et al. | 422/28 |
| 5,002,684 | 3/1991 | Beck | 252/105 |
| 5,252,243 | 10/1993 | Minns | 252/102 |

FOREIGN PATENT DOCUMENTS

| | | | |
|---|---|---|---|
| 1-163298 | 6/1989 | Japan | 252/102 |

OTHER PUBLICATIONS

Randlett, J. C. et al. Spotting, published by National Institute of Drycleaning, Silver Spring, Md., 1956, pp. 788 & 146 (no month available).

EPA 89110696.5, published Dec. 20, 1989.

*Primary Examiner*—Dennis Albrecht

*Attorney, Agent, or Firm*—Karen M. Dellerman

[57] ABSTRACT

An aqueous composition cleans and sanitizes carpets and the like. The composition contains (in percents by weight) from about 3 to about 15 percent peroxide, up to about 5% of volatile ammoniated substance, up to about 30% volatile wetting agent, and the balance water. The solution is substantially completely volatile so that it does not leave a soil harboring residue.

6 Claims, No Drawings

VOLATILE CARPET SANITIZING SHAMPOO CONTAINING HYDROGEN PEROXIDE

CROSS REFERENCE TO RELATED APPLICATIONS

This application is a continuation of U.S. patent application Ser. No. 07/887,446 filed May 21, 1992, now abandoned, which is a continuation-in-part of U.S. patent application Ser. No. 07/650,353 filed Feb. 4, 1991, now abandoned, which in turn is a continuation-in-part of U.S. patent application Ser. No. 07/462,919 filed Jan. 8, 1990, now U.S. Pat. No. 5,252,243, which in turn is a continuation of U.S. patent application Ser. No. 07/206,531, filed Jun. 14, 1988, now abandoned.

FIELD OF THE INVENTION

This invention relates generally to cleaning carpets and the like, and more particularly, to compositions which sanitize such carpets.

BACKGROUND OF THE INVENTION

As used herein, the term "volatile" means materials that tend to pass into the vapor state at conditions prevalent in human occupied facilities (room temperature (15°-30° C.) and prevalent atmospheric pressure).

As used herein, the term "sanitize" or "sanitized" means a 99.9% reduction of test bacteria over a scrubbed control as described in DIS/TSS-8, dated Feb. 6, 1979, of the United States Environmental Protection Agency, as modified Apr. 13, 1981, and May 27, 1981.

A major concern in the care of carpeting, besides basic cleanliness, is reducing microbial contaminants to safe levels (sanitizing) as determined by public health requirements. This is especially important in hospital and other health care facilities where the presence of unwanted bacteria may be detrimental to the health of convalescing patients. The United States Environmental Protection Agency (EPA) has outlined efficacy. data requirements for products bearing label claims for effectiveness as carpet sanitizers. These requirements are outlined in DIS/TSS-8, noted above.

While a number of materials may provide appropriate sanitizing efficacy, another important concern which these materials do not address is the presence of dirt-attracting residues. Such residues allow carpet to rather quickly become unsanitary because of the soil and bacteria which is attracted by the residue.

Sanitizing liquid carpet shampoos are known from, for example, U.S. Pat. No. 4,490,270 to Hackett et al. This patent discloses an aqueous solution for use in cleaning and sanitizing carpets and the like, consisting of surfactant, inorganic phosphate, glutaraldehyde, solvent and brightener.

The use of peroxide compounds for sterilization is known. U.S. Pat. No. 3,904,361 to Egger discloses the sterilization of packaging material by applying a film of sterilizing liquid which may include hydrogen peroxide. U.S. Pat. No. 4,512,951 to Koubek discloses a method for sterilizing medical articles by vapor penetration and direct liquid sterilant contact in which the vapor mixture includes hydrogen peroxide. U.S. Pat. No. 4,557,898 to Greene et al. discloses an aqueous acidic disinfecting and sterilizing composition which contains hydrogen peroxide claimed to be useful for disinfecting and sterilizing metal, ceramic and plastic surfaces. U.S. Pat. No. 4,943,414 to Jacobs et al. discloses a method and device for vapor sterilizing the lumen of medical instruments and the like. The liquid sterilant solution may contain hydrogen peroxide.

The use of peroxide containing solutions as in the treatment of fibrous articles is known. U.S. Pat. No. 3,607,760 to McIntyre discloses a solution, dilute in hydrogen peroxide, for removing pet stains from carpeting. U.S. Pat. No. 4,347,149 and U.S. Pat. No. 4,497,725, both to Smith et al., disclose a laundry bleaching composition which contains hydrogen peroxide. The patent discloses that when used as a bleaching composition, the solution is quite dilute. Incidentally, these patents also disclose that the bleaching agent may be used as a hard surface cleaner.

A carpet spot remover is known from co-owned U.S. patent application Ser. Nos. 07/462,919, filed Jan. 8, 1990, and 07/650,353, filed Feb. 4, 1991, now abandoned which have a similar or identical formula to the present invention. The use of that spot remover as a general cleaner on an entire installation of carpet or as a sanitizer is not known.

SUMMARY OF THE INVENTION

One embodiment of the present invention provides a two-part aqueous solution composition for use in cleaning and sanitizing carpets and the like that consists essentially of (in percents by weight), a first part comprising from about 3 to about 15 percent peroxide, and the balance water; and a second part comprising optionally up to about 5% of volatile ammoniated substance, up to about 60% volatile wetting agent, and the balance water.

Another embodiment of the present invention provides A method for sanitizing carpet and the like comprising (a) treating the carpet with an aqueous solution consisting essentially of in parts by weight of the total composition from about 3 to about 15 percent peroxide, up to 30% volatile wetting agent, optionally, a volatile ammoniated substance, and the balance water, said treating in an amount sufficient to comply with the Efficacy Data Requirements known as DIS/TSS-8, and (b) allowing the carpet to dry.

It is an object of the present invention to provide an improved carpet sanitizing composition.

It is another object of the present invention to provide an improved method for sanitizing carpets and the like.

Related objects and advantages will be apparent to those ordinarily skilled in the art to which the invention pertains after reading the following description of the invention.

DETAILED DESCRIPTION OF THE PREFERRED EMBODIMENTS

To promote an understanding of the principles of the present invention, descriptions of specific embodiments of the invention follow and specific language describes the same. It will nevertheless be understood that no limitation of the scope of the invention is thereby intended, and that such alterations and further modifications, and such further applications of the principles of the invention as discussed are contemplated as would normally occur to one ordinarily skilled in the art to which the invention pertains.

The present invention involves carpet sanitizing compositions and methods which comply with the EPA efficacy requirements for such. These compositions are essentially volatile so that, after sanitizing, there remains substantially no residue to harbor bacteria. In general, the compositions may contain peroxide, a volatile wetting agent, and an ammoniated substance.

The aqueous shampoo compositions of the present invention are mixtures of ingredients so that the solution applied to carpet has between about 3% and about 15% of a peroxide. Perferably, the composition contains up to 30% of a volatile wetting agent. Optionally, the composition may contain ammonia or other volatile ammoniated compounds.

Peroxides that are useful in the present invention include hydrogen peroxide or any compound which, in aqueous composition, yields hydrogen peroxide and is volatile so that it does not leave a residue. The preferred oxidizing agent is hydrogen peroxide.

Ammoniated substances useful in the present invention should be volatile under the conditions found in standard hospital and health care facilities. These substances include ammonia and tetrabutyl ammonia hydroxide, as well as certain other ammoniated substances. The suggested amounts of ammonia and other volatile ammoniated compounds should be within the range of about 0.1% to 5%.

Wetting agents useful in the present invention should be volatile as well. Generally, preferable wetting agents are miscible with water and organically based. Especially preferred are wetting agents that also have sanitizing ability. Two classes of useful wetting agents are glycols and lower aliphatic alcohols. Exemplary alcohols include water soluble alcohols containing up to 5 carbon atoms, such as methyl alcohol, ethyl alcohol, N-propyl alcohol, isopropyl alcohol, sec-butyl alcohol, and tert-butyl alcohol. The presently preferred alcohol is isopropyl alcohol. Exemplary glycols include glycerol, ethylene glycol, propylene glycol, and trimethylene glycol. The suggested amounts of wetting agent should be no more than 30%.

A first embodiment of the present invention is a two-part composition. The first part is an aqueous peroxide solution, and the second part is an aqueous solution containing a volatile wetting agent that is a sanitizer and, optionally, an ammoniated substance. The two parts are mixed prior to use to give a desired final concentration having between about 3% and about 15% peroxide.

The first part preferably contains between about 5% and 29% hydrogen peroxide, with the balance being deionized water. Preferably, the second part contains about 4% wetting agent, the balance being water and, optionally, the ammoniated substance.

The two-part system of the invention is preferably mixed just prior to application to greatly enhance the final composition stability. This two-part system is quite stable and does not require stabilizers. The parts are mixed to obtain, after mixture, about 3%-15% peroxide, up to about 30% wetting agent (preferably about 2%), and about 0.1% to 5% ammoniated substance.

The two parts may be provided in a number of ways. For example, the parts may be provided in two separate containers and mixed in equal parts (or as required to obtain the desired final formulation) in a third container soon before use. The mixture is then applied to the stained material according to the method described below. Alternatively, the two parts may be supplied in a single partitioned container where the partition prevents the parts from mingling prior to use. This type of container may be fitted with a spray nozzle which draws from each part and mixes the parts in the spray. Advantageously, this type of nozzle is provided with one-way valves to prevent the mixed solution from flowing back into the receptacles. Also, the two parts can be separately sprayed in appropriate volumes directly onto the stain.

Another embodiment of the present invention is an aqueous solution sanitizing composition. This composition contains from about 3% to about 15% peroxide, up to about 30% of a volatile wetting agent and, optionally, an ammoniated substance and, preferably, the balance water.

A third embodiment of the present invention involves a method of sanitizing using the sanitizing compositions above. This method includes applying the aqueous sanitizing compositions to carpet and the like to be sanitized. Since the components are all volatile, they do not leave a residue on the carpet, which would attract dirt and bacteria. Therefore, the carpet remains sanitized for a long period of time. Advantageously, in applying the sanitizer of the invention according to this method, standard carpet cleaning equipment which first applies the sanitizer and then suctions as much of the aqueous composition into a reservoir for disposal is preferable.

The sanitizer destroys substantially all bacteria and then evaporates without leaving a residue. After the treated carpet is allowed to air dry, i.e. dry under ambient conditions, it may be extracted with hot water to remove the dead bacteria.

In general, the present invention is useful on any synthetic fiber carpet or the like or natural fiber which is not alkaline sensitive. Examples of such fibers include those made from synthetic thermoplastic polymers which are capable of being formed into fibers, such as by melt extrusion, including polyolefins, for example, homopolymers of olefins such as low density polyethylene, high density polyethylene, polypropylene, and the like. Copolymers of olefins with other ethylenically unsaturated monomers such as ethylenepropylene copolymers and ethylenebutene copolymers and the like find particular application with the present invention.

Fibers made from polyamides also find particular application with the present invention. Examples of such polyamides include homopolyamides and copolyamides which are obtained by the polymerization of lactam of aminocaprionic acid or a copolymerization product from mixtures of diamines together with dicarboxylic acids or mixtures of lactams.

Typical polyamides include nylon 6, nylon 6,6, nylon 6,10, nylon 6,12, nylon 11, nylon 12, copolymers thereof, or mixtures thereof. Polyamides can also be copolymers of nylon 6 or nylon 6,6 and a nylon salt obtained by reacting a dicarboxylic acid component such as terephthalic acid, isophthalic acid, adipic acid, or sebacic acid with a diamine such as hexamethylenediamine or 1,4-bisaminomethylcyclohexane.

Fibers made from polyester also find particular application with the present invention. The preferred polyesters are the linear terephthalate polyesters, i.e., polyesters of a glycol containing from 2 to 20 carbon atoms and a dicarboxylic acid comprising at least about 75% terephthalic acid. The remainder, if any, of the dicarboxylic component may be any suitable dicarboxylic acid, such as sebacic acid, adipic acid, isophthalic acid, sulfonyl-1, 4-4-dibenzoic acid, or 2,8-dibenzofurandicarboxylic acid. Examples of linear terephthalate polyesters which may be employed include poly(ethylene terephthalate), poly(butylene terephthalate), poly(ethylene terephthalate/5-chloroisophthalate), poly- (ethylene terephthalate), poly(butylene terephthalate), poly(ethylene terephthalate/5-chloroisophthalate), poly(ethylene terephthalate/5-[sodium sulfo]-isophthalate), and poly(cyclohexane-1, 4-dimethylene terephthalate/hexahydroterephthalate).

The present invention is also useful with fibers made from polyacrylonitrile homopolymers and copolymers.

The invention will be described by reference to the following detailed examples. The Examples are set forth by way of illustration, and are not intended to limit the scope of the invention. In the examples, all parts are part by weight unless otherwise specified.

EXAMPLES

In the following examples, test carpets used are as follows:

Sample A is nylon 6 bulked continuous filament level loop at 29.1 ounces per square yard with a pile height of 0.156" and a density of 6727 ounces per cubic yard.

Sample B is nylon 6 spun yarn cut pile at 28.0 ounces per square yard with a pile height of 0.187" and a density of 5400 ounces per cubic yard.

Sample C is polypropylene bulked continuous filament cut pile at a weight at 10.86 ounces per square yard with a pile height of 0.25" and a density of 1562 ounces per cubic yard.

Preparation of Sanitizer According to the Present Invention

Part A: An aqueous solution is prepared containing 18.8% hydrogen peroxide and 81.2% deionized water.

Part B: An aqueous solution is prepared containing 1.3% saturated ammonia solution, 4.0% isopropanol and 94.7% deionized water.

Test Solution (Sanitizer): Part A and Part B were mixed in equal parts to give a solution having 9.8% hydrogen peroxide, 0.6% saturated ammonia, 2.0% isopropanol and 87.6% deionized water.

Procedure

Twelve 2×2 inch squares are cut from each test carpet type A, B and C. The 2"×2" squares are sterilized using steam in an autoclave at 121° C. and 15 psig. Achievement of the sterilization temperature is confirmed using a thermometer and sterile tape. The sterile tape turns from white to black when the autoclave reaches a correct sterilization temperature. Each Test Bacteria (Pseudomonas Aeroginosa, Staphylococcus Aureus, Enterbacter Aerogenes) is inoculated on four test squares of each carpet type. Two of these squares are sanitized and two are controls. The carpet containing the test bacteria is dried for 60 minutes at 35° C.

The Test Solution is prepared. The Test Solution is sprayed on the carpet at a rate of thirty milliliters per seventy-two square inches.

As a control, sterile water containing 0.01% isooctylphenoxy-polyethoxyethanol is applied in the same manner to 4 additional squares of each carpet type.

All test squares and controls remain at room temperature for 60 minutes. The test bacteria is extracted from each carpet square in neutralizer broth containing 1% of a suitable defoaming agent (Pluronic 25R2). Plate counts are performed in serial dilutions in neutralizer plate count agar. Results are as follows (average of two). The range represents the largest count per sample less the smallest count per sample.

TEST BACTERIA: PSEUDOMONAS AEROGINOSA

| Sample ID | Standard Plate Count ("SPC")* | Range |
|---|---|---|
| Control Carpet Sample A | 1,970,000 | 3,140,000 |
| Control Carpet Sample B | 4,850,000 | 1,500,000 |
| Control Carpet Sample C | 4,175,000 | 3,050,000 |
| Sanitized Carpet Sample A | <1 | <1 |
| Sanitized Carpet Sample B | <1 | <1 |
| Sanitized Carpet Sample C | <1 | <1 |

TEST BACTERIA: STAPHYLOCOCCUS AUREUS

| Sample ID | Standard Plate Count* | Range |
|---|---|---|
| Control Carpet Sample A | 6,996,000 | 3,110,000 |
| Control Carpet Sample B | 763,000 | 124,000 |
| Control Carpet Sample C | 6,500,000 | 5,000,000 |
| Sanitized Carpet Sample A | <1 | <1 |
| Sanitized Carpet Sample B | <1 | <1 |
| Sanitized Carpet Sample C | <1 | <1 |

TEST BACTERIA: ENTERBACTER AEROGENES

| Sample ID | Standard Plate Count* | Range |
|---|---|---|
| Control Carpet Sample A | 5,865,000 | 1,270,000 |
| Control Carpet Sample B | 2,915,000 | 770,000 |
| Control Carpet Sample C | 5,200,000 | 1,200,000 |
| Sanitized Carpet Sample A | <1 | <1 |
| Sanitized Carpet Sample B | <1 | <1 |
| Sanitized Carpet Sample C | <1 | <1 |

*per ml of extraction fluid

The Test Solution shows a nearly 100% reduction in bacterial growth of all three species inoculated onto three test carpets (A, B, and C) as described in the introduction. This meets the performance requirements set forth by the United States Environmental Protection Agency in accordance with test procedure DIS/TSS-8 developed and used by the EPA.

Although certain preferred embodiments of the invention have been herein described for illustrative purposes, it will be appreciated that various modifications and innovations of the procedures recited may be effected without departure from the basic principles which underlie the invention. Changes of this type are therefore deemed to lie within the spirit and scope of the invention.

What is claimed is:

1. The use of an aqueous solution composition for cleaning and sanitizing synthetic carpets and upholstery comprising:

(a) combining just prior to use two separate parts to make said aqueous solution composition wherein said parts consist essentially of:

a first part comprising from about 5 to about 29 percent peroxide, and the balance water; and a second part comprising up to about 10% of volatile ammoniated substance, up to about 60% of a lower aliphatic monohydric alcohol selected from the group consisting of methyl alcohol; ethyl alcohol; n-propyl alcohol; isopropyl alcohol; sec-butyl alcohol; tert-butyl alcohol: and mixtures thereof, and the balance water, said solution being substantially completely volatile;

wherein said combining is such that said aqueous solution composition contains from about 3 to about 15 percent peroxide, from about 2 to 30% of a lower aliphatic monohydric alcohol and from about 0.1 to 5% volatile ammoniated substance;

(b) contacting said synthetic carpet or upholstery with said aqueous solution composition; and (c) allowing the carpet or upholstery so contacted to dry substantially without deposition of a residue from said solution.

2. The use of claim 1 wherein in said combining the peroxide is hydrogen peroxide.

3. The use of claim 2 wherein in said combining about 20% peroxide is present in said first part.

4. The use of claim 1 wherein in said combining said lower aliphatic monohydric alcohol is present up to about 5% of said second part.

5. The use of use of claim 4 wherein in said combining said lower aliphatic monohydric alcohol is isopropyl alcohol.

6. The use of claim 1 wherein in said combining said ammoniated substance is ammonia present as about 1%.

* * * * *